(12) United States Patent
Gastaldo

(10) Patent No.: US 8,654,324 B2
(45) Date of Patent: Feb. 18, 2014

(54) DEVICE AND METHOD FOR INSPECTING SEMICONDUCTOR WAFERS

(75) Inventor: Philippe Gastaldo, Pontcharra (FR)

(73) Assignee: Altatech Semiconductor, Montbonnot-Saint-Martin (FR)

( * ) Notice: Subject to any disclaimer, the term of this patent is extended or adjusted under 35 U.S.C. 154(b) by 59 days.

(21) Appl. No.: 13/203,117

(22) PCT Filed: Feb. 23, 2010

(86) PCT No.: PCT/FR2010/000165
§ 371 (c)(1),
(2), (4) Date: Nov. 8, 2011

(87) PCT Pub. No.: WO2010/097523
PCT Pub. Date: Sep. 2, 2010

(65) Prior Publication Data
US 2012/0057155 A1 Mar. 8, 2012

(30) Foreign Application Priority Data
Feb. 25, 2009 (FR) .................................... 09 00862

(51) Int. Cl.
*G01N 21/00* (2006.01)
*G01N 21/95* (2006.01)
(52) U.S. Cl.
CPC .................................. *G01N 21/9501* (2013.01)
USPC ................................... 356/237.2; 356/237.5
(58) Field of Classification Search
CPC ........................... G01N 21/00; G01N 21/9501
USPC ............................................ 356/237.1–237.5
See application file for complete search history.

(56) References Cited

U.S. PATENT DOCUMENTS

| | | | |
|---|---|---|---|
| 6,580,502 B1 | 6/2003 | Kuwabara | |
| 6,917,421 B1 | 7/2005 | Wihl et al. | |
| 6,934,019 B2 * | 8/2005 | Geffen et al. | 356/237.4 |
| 7,477,401 B2 * | 1/2009 | Marx et al. | 356/609 |
| 2005/0030528 A1 * | 2/2005 | Geffen et al. | 356/237.1 |
| 2006/0109483 A1 * | 5/2006 | Marx et al. | 356/609 |
| 2008/0031509 A1 * | 2/2008 | Heiden et al. | 382/145 |
| 2008/0180656 A1 | 7/2008 | Meeks et al. | |
| 2010/0171962 A1 | 7/2010 | Ben-Levi et al. | |
| 2012/0314206 A1 * | 12/2012 | Spizig et al. | 356/72 |

OTHER PUBLICATIONS

French Search Report for PCT Application No. PCT/FR2010/000165 issued Jun. 6, 2010.

* cited by examiner

*Primary Examiner* — Michael P Stafira
(74) *Attorney, Agent, or Firm* — Meyertons, Hood, Kivlin, Kowert & Goetzel, P.C.; Eric B. Meyertons

(57) ABSTRACT

The invention relates to a device for inspecting the edge of semiconductor wafers, including a chromatic confocal microscope with a lighting pathway and an analysis pathway, the lighting pathway including a polychromatic light source, a slot and an axial chromatism objective lens comprising a lens at least made of a material having an Abbe number lower than 50, and the analysis pathway includes said objective lens, a chromatic filtering slot with a light intensity sensor in that order, the slot of the lighting pathway and the slot of the analysis pathway being provided at substantially the same optical distance from the edge of the wafer to be inspected.

15 Claims, 5 Drawing Sheets

DEVICE AND METHOD FOR INSPECTING SEMICONDUCTOR WAFERS

BACKGROUND OF THE INVENTION

1. Field of the Invention

The invention relates to the field of the inspection and monitoring of semiconductor wafers or substrates during or at the end of manufacture or during the production of integrated circuits.

2. Description of the Relevant Art

The tendency of semiconductor wafers to increase in diameter means that they have to be handled with extreme care and are ever more fragile. Moreover, the increasingly fine etching of designs on a semiconductor wafer makes each component of the wafer more and more prone to manufacturing defects.

The increase in the diameter of the substrates, the reduction in size of the designs and the efforts to achieve an increased yield during the manufacture of integrated circuits cause the manufacturers and substrate users to inspect the entire surface of the substrate comprising the upper surface, the lower surface and the cross-section.

The invention sets out to improve the situation.

SUMMARY OF THE INVENTION

A device for inspecting the edges of semiconductor wafers comprises a confocal chromatic microscope provided with a lighting pathway and an analysis pathway. The lighting pathway comprises a polychromatic light source, a slot and an objective lens with axial chromatism selected to have a chromatic aberration, comprising at least one lens made of a material having an Abbe number of less than 50. The analysis pathway comprises the said objective lens, a chromatic filtering slot and a light intensity sensor in that order. The slot of the lighting pathway and the slot of the analysis pathway are arranged substantially at the same optical distance from the wafer edge to be inspected. In other words, the said slots may be located at the same optical distance from the edge of the objective lens. In this way it is possible to filter spatially the wavelengths that are not focussed on the edge of the semiconductor wafer during the inspection.

The process for inspecting the edges of semiconductor wafers comprises steps during which the edge is illuminated with a polychromatic light source, the incident light beam passing through a slot and through an objective lens having an aberration, comprising at least one lens made of a material with an Abbe number of less than 50, and the reflected beam is collected after it has passed through said objective lens then through a chromatic filtering slot configured so as to spatially filter the wavelengths that are not focussed on the edge of the semiconductor wafer. This collection is carried out using a light intensity sensor.

BRIEF DESCRIPTION OF THE DRAWINGS

The invention will be more readily understood from a study of the detailed description of a number of embodiments by way of example which are in no way restrictive and are illustrated in the attached drawings, wherein.

DETAILED DESCRIPTION OF THE PREFERRED EMBODIMENTS

Figure 1:
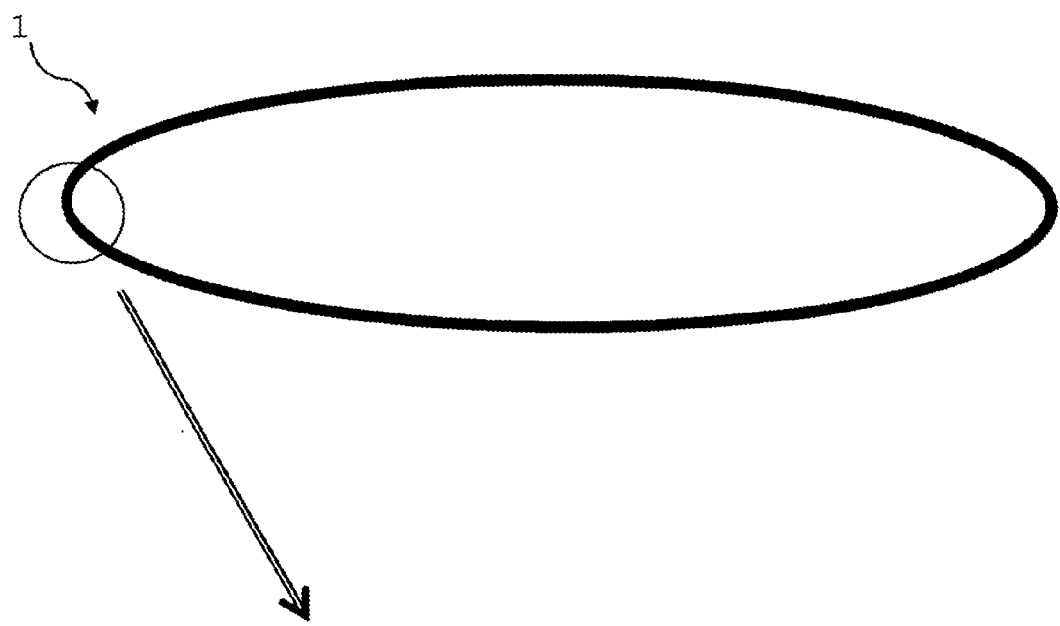
FIG. 1 is a diagrammatic view of a semiconductor wafer.
Figure 2:
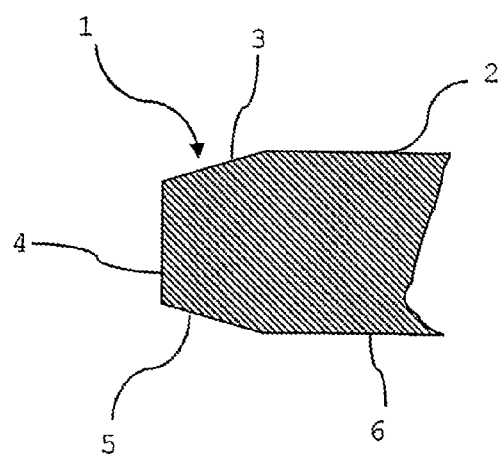
FIG. 2 shows a detail from FIG. 1.

Generally speaking, the inspection of the cross-section of a semiconductor substrate 1 is carried out by rotating the substrate in front of a viewing system of the matrix or linear camera type. By the substrate cross-section is meant the side 4 that is substantially perpendicular to the upper and lower surfaces of the substrate, the upper bevel 3 or chamfer, the lower bevel 5 or chamfer, the zone close to the upper edge 2 and the zone close to the lower edge 6, cf. FIGS. 1 and 2. The opposite surfaces of the substrate are conventionally referred to as the upper and lower surfaces, even when the substrate is in the vertical position, by reference to a horizontal position of the substrate when it is supported by a handling member such as a fork.

The limitation of conventional systems resides chiefly in the depth of field. In fact, the optical diffraction limits mean that it is very difficult to obtain strong magnification and great depth of field with a conventional optical system. This is particularly inconvenient when inspecting the cross-section of a substrate. On the one hand, as the cross-section is curved, the distance between the observation system and the surface to be inspected is not constant. This limits the possible magnification. On the other hand, the inspection of the surface is carried out during rotation of the substrate. In order to ensure that the distance between the object and the objective lens is as stable as possible, the movement is carried out at low speed with an extremely precise and stable handling system. This requires a slow rate of measurement and expensive monitoring equipment.

For checks involving sampling or for analysing zones limited to a small part of the edge surface, it is possible to use high-performance slot inspection systems with a small observation field and strong magnification. Of these slow systems, confocal microscopy is one that may be chosen.

However, the rate of capture of confocal microscopy equipment means that it cannot be used for the systematic inspection of mass production such as that carried out in the semiconductor industry.

Now, the Applicant has found that the increase in the diameter of the substrates increases the internal mechanical stresses which they undergo and consequently increases the risk of propagation of defects, for example microscopic cracks on the edge of the substrate. Moreover, the increased yield, in the sense of the number of chips per substrate, the diameter being equal, results in the chips being arranged close to the edges. The inspection of the edges therefore takes on more and more importance.

The publications WO 88/10406 and EP 0142464 show a technique of chromatic analysis through a dispersive optical system for measuring the distance(s) between a sensor and an object. These techniques are very slow.

The publication FR 2 805 342 relates to the surface inspection of semiconductor substrates with a function of measuring surface reliefs.

Chromatic coding is used in distance measurement in order to adjust the focus on equipment intended for photolithography in the semiconductor field. The measurement of thickness or distance requires a chromatic analysis of reflected light in order to convert this information into a geometric parameter of the object measured. This conversion is slow.

The invention makes use of confocal chromatic microscopy based on confocal microscopy and the use of the chromatic aberration in the optical system used. In general, a confocal microscope mechanically readjusts the focussing point of the optical device and from this it deduces the morphology of the surface. This mechanical readjustment is slow and liable to cause breakdowns. Moreover, as the movements are generally associated with friction, they often turn out to be the source of particles, which must be avoided in an environment for producing microelectronic components.

Thanks to the invention, a narrow range of well focussed wavelengths is used, by means of which a clear image is obtained. By analysing the wavelength, if desired, it is possible to determine the distance between the confocal chromatic sensor and the object being analysed. With an optical system with a strong chromatic aberration comprising at least one lens made of a material having an Abbe number of less than 50, possibly even 35, different focuses are produced for different wavelengths. This results in a spatial spreading out of the focal point and a great depth of field. The depth of field may be up to several millimetres.

By keeping the wavelength or a narrow range of wavelengths corresponding to the well-focussed wavelength, an optical autofocus system is obtained. This autofocus system does not require any mechanical movement. This is achieved by means of the slots located at the same optical distance from the surface that is to be inspected or from the objective lens, in so far as the objective lens belongs to both the lighting pathway and the analysis pathway. Thus it is possible to achieve a multipoint capture, each having the advantageous properties mentioned above. The separation of the lighting pathway and analysis pathway may be obtained by means of a semi-reflective plate located between the slot and the objective lens for the lighting pathway and between the objective lens and the chromatic filtering slot for the analysis pathway. The slot forms a linearising element.

The light source may comprise a set of light-emitting diodes, for example in the form of a strip or bar, and a diffuser. The diffuser may comprise ground glass.

The device may comprise a processing unit connected to an output of the sensor for receiving and analysing a light intensity signal. It is possible to provide a plurality of light intensity sensors for inspecting a plurality of facets of the edge, while the processing unit may comprise an assembler of output data from the light intensity sensors generating a file of inspection results for said plurality of sensors. The processing unit may comprise an edge defect discriminator, generating a grading according to the type of defect, its position, reflectivity, shape or size.

In one embodiment, the device comprises a chromatic analyser of the light that is diffused or reflected back by an edge of the semiconductor wafer with an output connected to the processing unit. The processing unit then comprises an extractor generating data for the distance between the objective lens and the edge of the semiconductor wafer.

The objective lens may have an optical diameter of less than 100 mm, which by being less bulky will enable the system to be integrated in a restricted space.

The surface to be inspected is arranged at a spacing within the chromatic aberration zone, in other words at a spacing between the wavelength of the incident light having the shortest focus and the wavelength of the incident light having the longest focus. The device makes it possible to inspect a cross-section of the edge of the substrate, independently of any focus adjusting mechanism. By continuous measurement of the cross-section during the rotation of the substrate it is possible to produce an image of the complete periphery of the substrate.

The inspection device uses the light amplitude information supplied by the sensor to offer a grey-scale image with economical equipment as well as a very fast capture, thus making it possible to obtain a system that is compatible with mass production. The device has an automatic autofocus function which makes it particularly simple, quick and reliable, particularly compared with conventional imaging systems. The device means that it is possible to observe a large field with points whose distance from the optical objective lens may vary more than with a conventional imaging system having the same magnification.

Optionally, the topographical measurement by chromatic analysis of the reflected light may be carried out for applications that are more precise and at a slower rate than analysis of detected defects after the event. The topographical measurement may also be used to quantify the edge drop information which is of particular interest for substrates that have been reconditioned and hence reground.

The position of the objective lens in relation to the surface to be inspected may be situated between several millimetres and several centimetres apart. This makes it possible to free up the space close to the substrate, this space generally being used for the handling of the substrate by one or more robots. In order to collect the maximum light for the given numerical aperture, it will nevertheless be desirable to maintain a short distance between the surface to be inspected and the objective.

The speed of rotation of the substrate may be between 0.1 and 10 rpm for a substrate 300 mm in diameter, for example between 1 and 10 rpm for light intensity analysis. This speed of rotation will have to be adjusted for a substrate of a different diameter in order to maintain a similar linear velocity, for example in the range between 0.1 and 10 metres per second, more particularly between 1 and 10 metres per second for light intensity analysis.

The resolution of the sensor may be between 128 and 10,000 pixels. The resolution may be adapted to the size of the defects being studied and the desired rate. The light source may comprise a xenon arc lamp, an incandescent lamp, a halogen lamp or a light-emitting diode source. Light-emitting diodes are advantageous in terms of service life, low energy consumption and low heating.

The incident light generated by the source then passes through the slot in the lighting pathway to linearise the beam. The unit comprising the light source and the slot in the incident pathway constitutes a linear light source. The incident beam then passes through a semi-reflective plate and then through the objective lens before reaching the surface to be inspected. The beam reflected by the surface to be inspected passes through the objective lens then through the semi-reflective plate and exits from it along an axis that is distinct from the axis of the incident pathway.

The reflected beam then passes through the chromatic filtering slot providing spatial filtering of the wavelengths that are not focussed on the surface to be inspected, resulting in an improvement in the clarity of the image. Downstream of the chromatic filtering slot, the reflected beam is essentially made up of the focussed wavelength or the narrow range of focussed wavelengths and therefore provides a clear image. The higher the axial chromatism of the objective lens, the more a difference in wavelength results in a considerable difference in the focussing distance. The reflected beam then reaches the light intensity sensor. The output from the light intensity sensor is connected to the processing unit.

Figure 3:
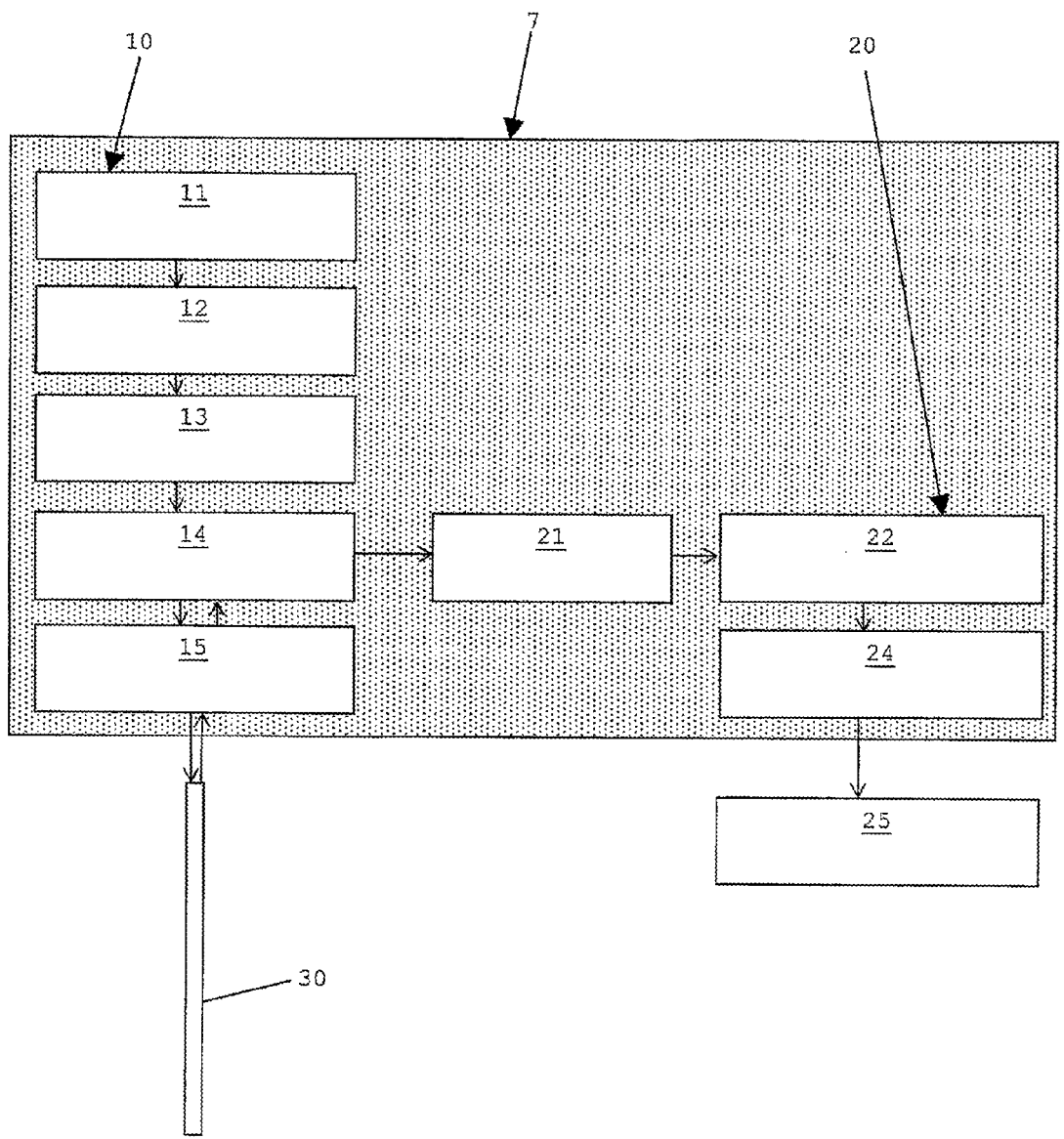
FIG. 3 is a diagrammatic view of a device for inspecting the edges of semiconductor wafers.

As can be seen in FIG. 3, the confocal chromatic microscope 7 comprises a lighting pathway 10 for illuminating an object 30 that is to be inspected, for example the edge of a semiconductor substrate, and an analysis pathway 20 supplying an output signal for a processing and analysing unit 25.

The lighting pathway 10 and the analysis pathway 20 comprise common parts, notably a semi-reflective plate 14 and an objective lens 15.

The lighting pathway 10 may comprise a broad-spectrum source 11 emitting a light beam, a spatial filtering slot 12 receiving said light beam, a optical collimator 13 comprising one or more lenses, said semi-reflective plate 14 and said objective lens 15. The semi-reflective plate 14 receives the incident beam from the optical collimator 13. The incident beam is directed towards the objective lens 15 from the output of the semi-reflective plate 14. The objective lens 15 has strong axial chromatism, for example with at least one lens made of a material characterised by a chromatic aberration with an Abbe number of less than 50. By way of example, the Abbe number may be equal to 35. The incident beam reaches the object to be inspected 30 after leaving the objective lens 15. The source 11 may comprise a strip of diodes 11a, a diffuser 11a and an output lens 11c.

The analysis pathway 20 comprises the said objective lens with strong axial chromatism 15, the semi-reflective plate 14 transmitting the reflected beam along an axis that is different from the input axis of the incident beam, towards a optical focussing device which will perform the opposite function to the optical collimator 13, operating according to the principle of the inverse return of light. The analysis pathway 20 also comprises a spatial filtering slot 22 arranged downstream of the focusing device 21. The slot 22 is also arranged at a distance from the object to be inspected 30 that is equal to the distance between the spatial filtering slot 12 of the lighting pathway 10 and the said object that is to be inspected 30.

Downstream of the spatial filtering slot 22 the analysis pathway 20 comprises a linear sensor 24 arranged in the path of the reflected beam. The linear sensor 24 may take the form of a set of sensor elements arranged in a strip. The sensor elements may be of the CCD or CMOS type. The output of the microscope 7 downstream of the sensor 24 is connected to a processing and analysing unit 25 illustrated in more detail in FIG. 6. Thanks to the presence of the spatial filtering slots 12 and 22 and the strong axial chromatism of the objective 15, the wavelengths that are not focussed on the surface of the object to be inspected 30 are filtered, by reason of their spatial offset in relation to the focussed wavelength, this offset being greater, the higher the axial chromatism of the objective lens 15. At the exit from the spatial filtering slot 22 of the analysis pathway 20, the filtered reflected beam comprises a narrow range of wavelengths that is substantially centred on the focussed wavelength, resulting in a very clear image and giving rise to the fact that the filtered reflected beam is representative of the defects in the inspected surface of the object 30.

In this embodiment, the microscope 7 carries out a measurement of the reflectivity of the surface of the object 30 that is to be inspected. Variations in reflectivity are representative of defects in the inspected surface. From these it is possible to deduce relatively precise information as to the size and type of defects. In the embodiment shown in FIG. 4, the analysis pathway 20 of the microscope 7 also comprises a dispersive element 23 arranged between the spatial filtering slot 22 and the sensor 24 in the path of the filtered reflected beam. The dispersive element 23 will have the function of spatially separating the wavelengths. The spectrum thus obtained will be projected onto a sensor, and the information as to the most intense wavelength will then be available and will give an image of the optimum focal length. The dispersive element 23 may be a diffraction network. The microscope 7 then provides, at the output, a signal representing the local distance of the microscope 7 from the inspected surface of the object 30, from which the topography of the inspected surface is deduced. A processing unit for the chromatic information carries out a conversion of the wavelength into the distance between the edge of the wafer to be inspected and the objective lens of the sensor. This embodiment provides a signal that is relatively difficult to process. This may prove useful for carrying out monitoring on samples or on semiconductor substrates having defects detected by other means, for example using a microscope 7 according to the embodiment in FIG. 3, which is capable of being integrated into a production line for semiconductor substrates.

Figure 4:
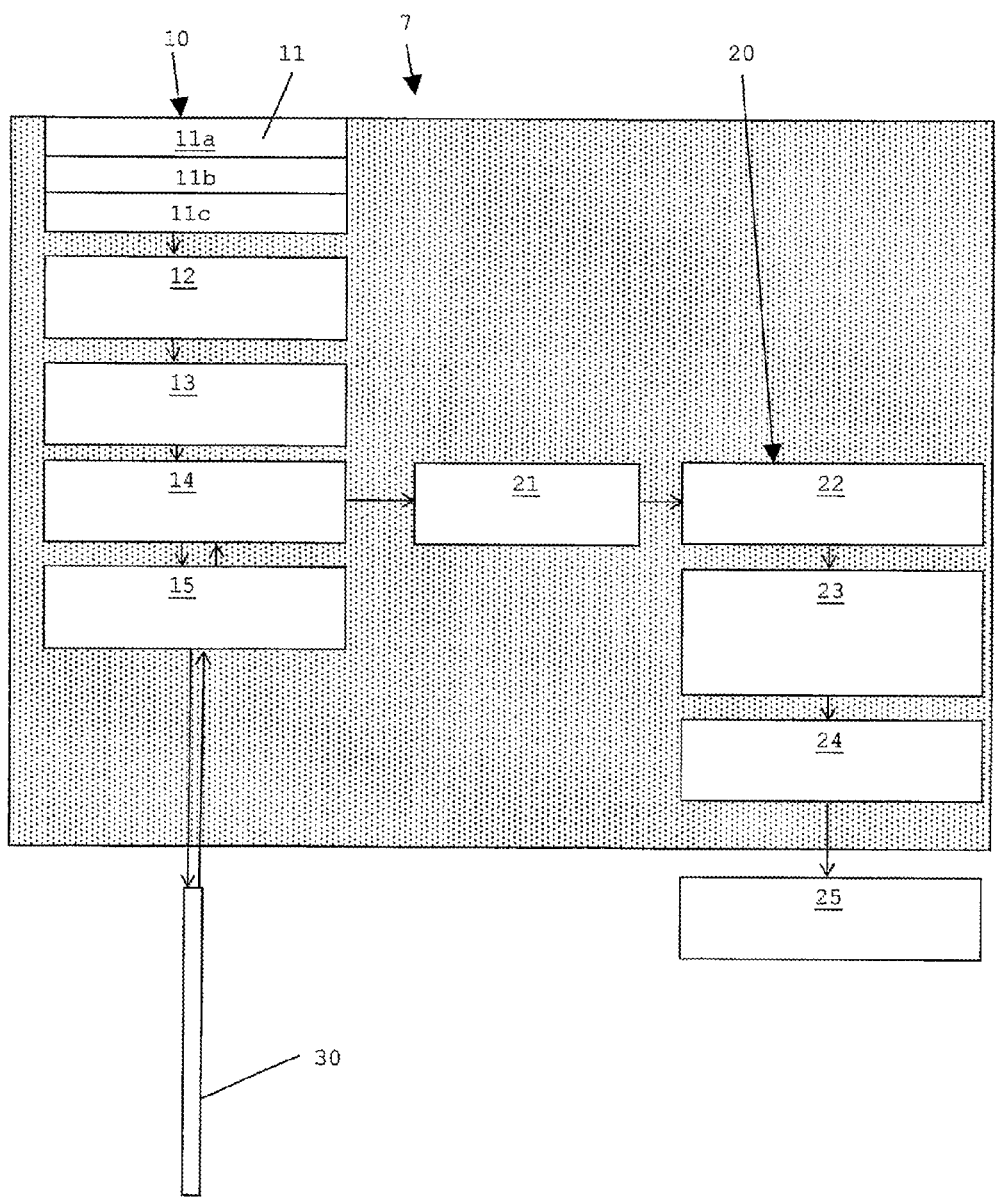
FIG. 4 is a variant of FIG. 3.

It is therefore possible to provide a microscope according to the embodiment in FIG. 3 that is arranged on the production line and inspects a large number, or possibly all, of the semiconductor substrates manufactured and a microscope according to the embodiment in FIG. 4 for inspecting semiconductor substrates having defects that have already been detected, this inspection possibly being 2 to 10 times slower than the previous one. The microscope according to the embodiment in FIG. 4 is then arranged away from the production line so as to receive the semiconductor substrates selected for their defects.

Figure 5:
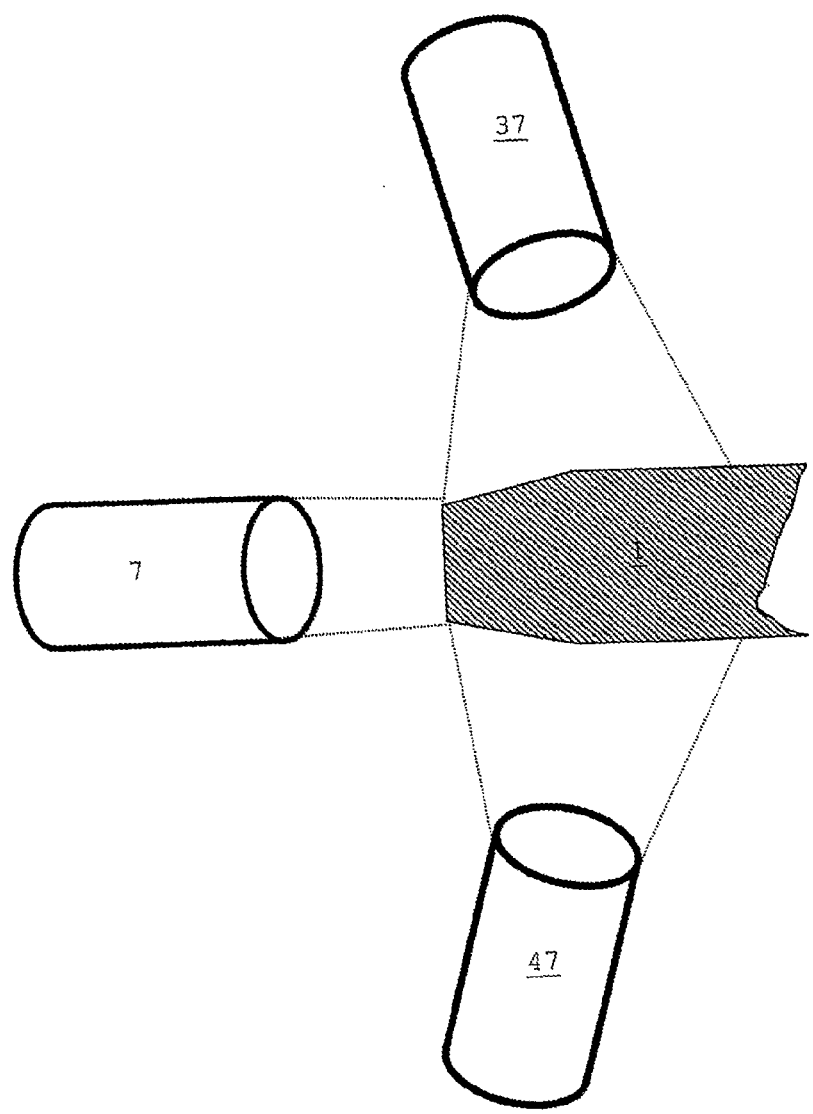
FIG. 5 is a diagrammatic view of an inspection device according to one embodiment.
Figure 6:
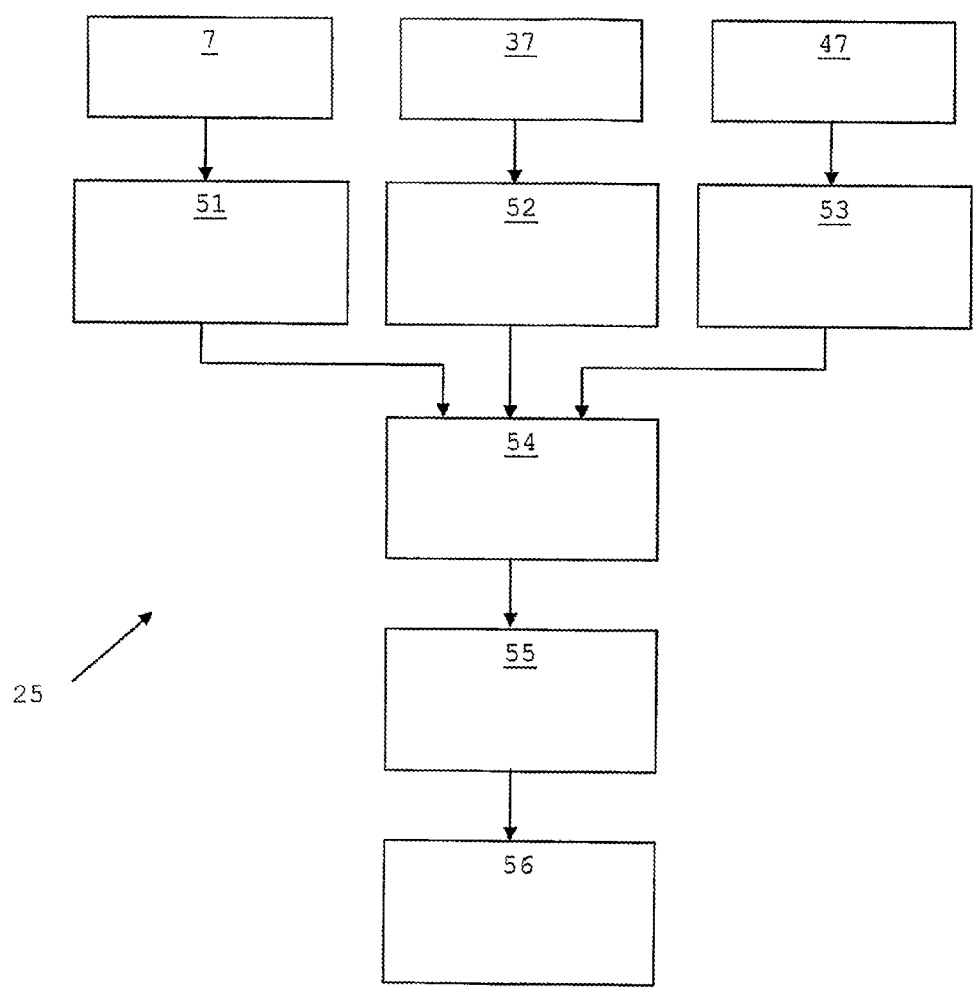
FIG. 6 is a diagrammatic view of a processing unit.

In the embodiment shown in FIG. 5, a plurality of microscopes 7, 37 and 47 are arranged for inspecting the edge of a semiconductor substrate (1). The microscopes 7, 37 and 47 may be in accordance with the embodiment in FIG. 3. The microscope 7 is positioned facing the side 4 of the substrate 1. The microscope 37 is arranged above the substrate 1 for inspecting the upper bevel 3 and the zone close to the upper edge 2. The microscope 47 is arranged underneath the substrate 1 for inspecting the lower bevel 5 and the zone close to the lower edge 6. The outputs of the microscopes 7, 37 and 47 may be connected to a common processing and analysing unit, as shown in FIG. 6.

The processing and analysing unit 25 comprises a plurality of capture cards, three in this instance. Each capture card 51, 52, 53 is connected to the output of a confocal chromatic microscope 7, 37, 47. The processing and analysing unit 25 also comprises an image reconstructing member 54 configured so as to generate an image from the images supplied at the output by the capture cards 51, 52, 53. The image reconstructing member proceeds to compare the upper end of the image of the side 4 with the lower end of the image of the upper bevel 3 and to compare the lower edge of the image of the side 4 with the upper edge of the image of the lower bevel 5. The image reconstructing member 54 detects any overlap from the results of the comparison and an assembly.

The processing and analysing unit 25 comprises one or more image processing means 55, for example in the form of software, for assisting with the detection of defects. The image processing means 55 may carry out operations of expansion, erosion, contour, etc. Moreover, the image processing means 55 may comprise a library of defects and a comparator for comparing the suspected defects with known defects stored in the library. The image processing means 55 are configured so as to generate at their output a file of results, notably in the form of an image file.

In another embodiment, it is possible to have processing of the images before reconstruction, thus allowing processing assisted by a smaller image size. A combination of the results will produce a synthesis results file.

The invention claimed is:

1. Multipoint device for inspecting the edges of semiconductor wafers during movement, comprising: a confocal chromatic microscope provided with a lighting pathway and an analysis pathway, the lighting pathway comprising a polychromatic light source, a slot and an objective lens with axial chromatism comprising at least one lens made of a material having an Abbe number of less than 50, and the analysis pathway comprising the said objective lens, a chromatic filtering slot and a linear light intensity sensor in that order, the slot of the lighting pathway and the slot of the analysis pathway being arranged substantially at the same optical distance from the edge of the wafer to be inspected.

2. Device according to claim 1, wherein the slot of the lighting pathway forms a linearization means.

3. Device according to claim 1, wherein the light source comprises a set of light-emitting diodes and a diffusion member.

4. Device according to claim 1, comprising a processing unit connected to an output of the sensor for receiving and analyzing a light intensity signal.

5. Device according to claim 1, comprising a plurality of microscopes for inspecting a plurality of facets of said edge, a processing unit comprising an assembler of output data from said light intensity sensors generating an inspection results file for said plurality of sensors.

6. Device according to claim 4, wherein the processing unit comprises a defect discriminator for said edge, generating a grading according to the type of defect, its position and its size.

7. Device according to claim 4, comprising a chromatic analyzer of the light diffused or reflected back by an edge of a semiconductor wafer with an output connected to the processing unit, the processing unit comprising an extractor that generates data for the distance between the objective lens and the edge of the semiconductor wafer.

8. Device according to one of the preceding claims, wherein the said objective lens has an optical diameter of less than 100 mm.

9. Device according to claim 1, comprising a semireflective plate arranged between the slots and the objective lens.

10. Device according to claim 1, wherein the analysis pathway comprises a dispersive element for spatially discriminating the light collected according to the wavelength.

11. Device according to claim 10, comprising a processing unit for the chromatic data forming a converter of the wavelength into the distance between the edge of the wafer to be inspected and the objective lens of the sensor.

12. Process for inspecting the edges of semiconductor wafers during movement, wherein the said edge is illuminated by a polychromatic light source, the incident beam passing through a slot and through an objective lens wherein the materials of at least one lens have a chromatic aberration with an Abbe number of less than 50, and the reflected beam is collected after it has passed through said objective lens then through a chromatic filtering slot configured to spatially filter the wavelengths not focused on the edge of the semiconductor wafer, the collection being carried out by a linear light intensity sensor.

13. Process according to claim 12, wherein the intensity of the beam collected is analyzed in order to deduce from it the defects in said edge.

14. Process according to claim 12, wherein the reflected light passes through a dispersive element producing a spatial spreading out of the collected light according to its wavelength.

15. Process according to claim 14, wherein a processing unit for the chromatic data converts at least one wavelength into the distance between the edge of the wafer to be inspected and the objective lens of the light intensity sensor.

* * * * *